(12) United States Patent
Lurie et al.

(10) Patent No.: US 8,151,790 B2
(45) Date of Patent: Apr. 10, 2012

(54) VOLUME EXCHANGER VALVE SYSTEM AND METHOD TO INCREASE CIRCULATION DURING CPR

(75) Inventors: Keith G. Lurie, Minneapolis, MN (US); Anja Köhler Metzger, Stillwater, MN (US)

(73) Assignee: Advanced Circulatory Systems, Inc., Eden Prairie, MN (US)

( * ) Notice: Subject to any disclaimer, the term of this patent is extended or adjusted under 35 U.S.C. 154(b) by 1184 days.

(21) Appl. No.: 11/871,879

(22) Filed: Oct. 12, 2007

(65) Prior Publication Data

US 2008/0257344 A1    Oct. 23, 2008

Related U.S. Application Data

(60) Provisional application No. 60/912,891, filed on Apr. 19, 2007.

(51) Int. Cl.
*A62B 9/02* (2006.01)

(52) U.S. Cl. ......... 128/200.24; 128/205.24; 128/207.16; 128/204.18; 128/204.23; 128/207.15

(58) Field of Classification Search ............ 128/205.24, 128/207.16, 204.18, 204.23, 207.15, 200.24
See application file for complete search history.

(56) References Cited

U.S. PATENT DOCUMENTS

| | | |
|---|---|---|
| 2,774,346 A | 12/1956 | Halliburton |
| 3,077,884 A | 2/1963 | Batrow et al. |
| 3,191,596 A | 6/1965 | Bird et al. |
| 3,216,413 A | 11/1965 | Mota |
| 3,307,541 A | 3/1967 | Hewson |
| 3,459,216 A | 8/1969 | Bloom et al. |
| 3,515,163 A | 6/1970 | Freeman |
| 3,662,751 A | 5/1972 | Barkalow et al. |
| 3,669,108 A | 6/1972 | Sundblom et al. |
| 3,794,043 A | 2/1974 | McGinnis |
| 3,815,606 A | 6/1974 | Mazal |
| 3,834,383 A | 9/1974 | Weigl et al. |
| 3,875,626 A | 4/1975 | Tysk et al. |
| 3,933,171 A | 1/1976 | Hay |
| 4,041,943 A | 8/1977 | Miller |
| 4,077,404 A | 3/1978 | Elam |
| 4,166,458 A | 9/1979 | Harrigan |
| 4,226,233 A | 10/1980 | Kritzer |
| 4,259,951 A | 4/1981 | Chernack et al. |
| 4,298,023 A | 11/1981 | McGinnis |
| 4,316,458 A | 2/1982 | Hammerton-Fraser |

(Continued)

FOREIGN PATENT DOCUMENTS

CA    668771    8/1963

(Continued)

OTHER PUBLICATIONS

PCT International Search Report and Written Opinion mailed Sep. 23, 2008, International Application No. PCT/US08/60367, 11 pages.

(Continued)

*Primary Examiner* — Steven Douglas

(74) *Attorney, Agent, or Firm* — Kilpatrick Townsend & Stockton LLP

(57) ABSTRACT

A method for regulating gas flows into and out of a patient includes repetitively forcing respiratory gases out of the lungs. Respiratory gases are prevented from entering back into the lungs during a time between when respiratory gases are forced out of the lungs. Periodically, an oxygen-containing gas is supplied to the lungs.

11 Claims, 8 Drawing Sheets

U.S. PATENT DOCUMENTS

| | | |
|---|---|---|
| 4,320,754 A | 3/1982 | Watson et al. |
| 4,349,015 A | 9/1982 | Alferness |
| 4,397,306 A | 8/1983 | Weisfeldt et al. |
| 4,424,806 A | 1/1984 | Newman et al. |
| 4,446,864 A | 5/1984 | Watson et al. |
| 4,449,526 A | 5/1984 | Elam |
| 4,481,938 A | 11/1984 | Lindley |
| 4,533,137 A | 8/1985 | Sonne |
| 4,601,465 A | 7/1986 | Roy |
| 4,809,683 A | 3/1989 | Hanson |
| 4,827,935 A | 5/1989 | Geddes et al. |
| 4,881,527 A | 11/1989 | Lerman |
| 4,898,166 A | 2/1990 | Rose et al. |
| 4,898,167 A | 2/1990 | Pierce et al. |
| 4,928,674 A | 5/1990 | Halperin et al. |
| 5,014,698 A | 5/1991 | Cohen |
| 5,016,627 A | 5/1991 | Dahrendorf |
| 5,050,593 A | 9/1991 | Poon |
| 5,056,505 A | 10/1991 | Warwick et al. |
| 5,109,840 A | 5/1992 | Daleidon |
| 5,163,424 A | 11/1992 | Kohnke |
| 5,184,620 A | 2/1993 | Cudahy et al. |
| 5,193,544 A | 3/1993 | Jaffe |
| 5,217,006 A | 6/1993 | McCulloch |
| 5,235,970 A | 8/1993 | Augustine |
| 5,263,476 A | 11/1993 | Henson |
| 5,295,481 A | 3/1994 | Geeham |
| 5,301,667 A | 4/1994 | McGrail et al. |
| 5,305,743 A | 4/1994 | Brain |
| 5,316,907 A | 5/1994 | Lurie |
| 5,355,879 A | 10/1994 | Brain |
| 5,359,998 A | 11/1994 | Lloyd |
| 5,377,671 A | 1/1995 | Biondi et al. |
| 5,392,774 A | 2/1995 | Sato |
| 5,398,714 A | 3/1995 | Price |
| 5,423,772 A | 6/1995 | Lurie |
| 5,437,272 A | 8/1995 | Fuhrman |
| 5,452,715 A | 9/1995 | Boussignac |
| 5,454,779 A | 10/1995 | Lurie et al. |
| 5,490,820 A | 2/1996 | Schock et al. |
| 5,492,116 A | 2/1996 | Scarberry et al. |
| 5,496,257 A | 3/1996 | Kelly |
| 5,517,986 A | 5/1996 | Starr et al. |
| 5,549,581 A | 8/1996 | Lurie |
| 5,551,420 A | 9/1996 | Lurie et al. |
| 5,588,422 A | 12/1996 | Lurie |
| 5,618,665 A | 4/1997 | Lurie |
| 5,628,305 A | 5/1997 | Melker |
| 5,632,298 A | 5/1997 | Artinian |
| 5,643,231 A | 7/1997 | Lurie |
| 5,645,522 A | 7/1997 | Lurie et al. |
| 5,657,751 A | 8/1997 | Karr, Jr. |
| 5,692,498 A | 12/1997 | Lurie et al. |
| 5,697,364 A | 12/1997 | Chua et al. |
| 5,704,346 A | 1/1998 | Inoue |
| 5,722,963 A | 3/1998 | Lurie |
| 5,730,122 A | 3/1998 | Lurie |
| 5,735,876 A | 4/1998 | Kroll et al. |
| 5,738,637 A | 4/1998 | Kelly et al. |
| 5,782,883 A | 7/1998 | Kroll et al. |
| 5,814,086 A | 9/1998 | Hirschberg et al. |
| 5,827,893 A | 10/1998 | Lurie |
| 5,919,210 A | 7/1999 | Lurie |
| 5,927,273 A | 7/1999 | Federowicz et al. |
| 5,937,853 A | 8/1999 | Ström |
| 5,977,091 A | 11/1999 | Nieman et al. |
| 5,984,909 A | 11/1999 | Lurie |
| 6,001,085 A | 12/1999 | Lurie |
| 6,029,667 A | 2/2000 | Lurie |
| 6,062,219 A | 5/2000 | Lurie et al. |
| 6,078,834 A | 6/2000 | Lurie |
| 6,155,257 A | 12/2000 | Lurie et al. |
| 6,174,295 B1 | 1/2001 | Cantrell et al. |
| 6,224,562 B1 | 5/2001 | Lurie et al. |
| 6,234,985 B1 | 5/2001 | Lurie et al. |
| 6,277,107 B1 | 8/2001 | Lurie |
| 6,312,399 B1 | 11/2001 | Lurie et al. |
| 6,425,393 B1 | 7/2002 | Lurie et al. |
| 6,459,933 B1 | 10/2002 | Lurie et al. |
| 6,463,327 B1 | 10/2002 | Lurie et al. |
| 6,486,206 B1 | 11/2002 | Lurie |
| 6,526,973 B1 | 3/2003 | Lurie et al. |
| 6,536,432 B2 | 3/2003 | Truschel |
| 6,578,574 B1 | 6/2003 | Kohnke |
| 6,587,726 B2 | 7/2003 | Lurie et al. |
| 6,604,523 B2 | 8/2003 | Lurie et al. |
| 6,656,166 B2 | 12/2003 | Lurie |
| 6,776,156 B2 | 8/2004 | Lurie et al. |
| 6,792,947 B1 | 9/2004 | Bowden |
| 6,863,656 B2 | 3/2005 | Lurie |
| 6,935,336 B2 | 8/2005 | Lurie et al. |
| 6,938,618 B2 | 9/2005 | Lurie et al. |
| 6,986,349 B2 | 1/2006 | Lurie |
| 7,032,596 B2 | 4/2006 | Thompson et al. |
| 7,044,128 B2 | 5/2006 | Lurie |
| 7,082,945 B2 | 8/2006 | Lurie |
| 7,174,891 B2 | 2/2007 | Lurie et al. |
| 7,185,649 B2 | 3/2007 | Lurie |
| 7,195,012 B2 | 3/2007 | Lurie |
| 7,195,013 B2 | 3/2007 | Lurie |
| 7,204,251 B2 | 4/2007 | Lurie |
| 7,210,480 B2 | 5/2007 | Lurie et al. |
| 7,226,427 B2 | 6/2007 | Steen |
| 7,275,542 B2 | 10/2007 | Lurie et al. |
| 7,311,668 B2 | 12/2007 | Lurie et al. |
| 7,682,312 B2 | 3/2010 | Lurie |
| 7,766,011 B2 | 8/2010 | Lurie |
| 7,836,881 B2 | 11/2010 | Lurie et al. |
| 7,899,526 B2 | 3/2011 | Benditt et al. |
| 2001/0029339 A1 | 10/2001 | Orr et al. |
| 2002/0029030 A1 | 3/2002 | Lurie et al. |
| 2002/0069878 A1 | 6/2002 | Lurie et al. |
| 2002/0104544 A1 | 8/2002 | Ogushi et al. |
| 2002/0170562 A1 | 11/2002 | Lurie et al. |
| 2002/0188332 A1 | 12/2002 | Lurie et al. |
| 2003/0000526 A1 | 1/2003 | Gobel |
| 2003/0037784 A1 | 2/2003 | Lurie |
| 2003/0062040 A1 | 4/2003 | Lurie |
| 2003/0062041 A1 | 4/2003 | Keith et al. |
| 2003/0192547 A1 | 10/2003 | Lurie et al. |
| 2004/0016428 A9 | 1/2004 | Lurie |
| 2004/0058305 A1 | 3/2004 | Lurie et al. |
| 2004/0200473 A1 | 10/2004 | Lurie |
| 2004/0200474 A1 | 10/2004 | Lurie |
| 2004/0211415 A1 | 10/2004 | Lurie |
| 2004/0211416 A1 | 10/2004 | Lurie |
| 2004/0211417 A1 | 10/2004 | Lurie |
| 2004/0231664 A1 | 11/2004 | Lurie |
| 2005/0016541 A1 | 1/2005 | Lurie et al. |
| 2005/0126567 A1 | 6/2005 | Lurie et al. |
| 2005/0165334 A1 | 7/2005 | Lurie et al. |
| 2005/0199237 A1 | 9/2005 | Lurie et al. |
| 2005/0217677 A1 | 10/2005 | Lurie |
| 2005/0267381 A1 | 12/2005 | Benditt |
| 2006/0089574 A1 | 4/2006 | Paradis |
| 2007/0021683 A1 | 1/2007 | Benditt et al. |
| 2007/0221222 A1 | 9/2007 | Lurie |
| 2007/0277826 A1 | 12/2007 | Lurie |
| 2008/0047555 A1 | 2/2008 | Lurie et al. |
| 2008/0108905 A1 | 5/2008 | Lurie |
| 2008/0255482 A1 | 10/2008 | Lurie |
| 2008/0257344 A1 | 10/2008 | Lurie et al. |
| 2009/0020128 A1 | 1/2009 | Metzger et al. |
| 2009/0277447 A1 | 11/2009 | Voss et al. |
| 2010/0179442 A1 | 7/2010 | Lurie |
| 2010/0319691 A1 | 12/2010 | Lurie et al. |

FOREIGN PATENT DOCUMENTS

| | | |
|---|---|---|
| CA | 2077608 A1 | 3/1993 |
| DE | 24 53 490 A1 | 5/1975 |
| EP | 0 029 352 A1 | 5/1981 |
| EP | 0 139 363 A | 5/1985 |
| EP | 0 245 142 A1 | 11/1987 |
| EP | 0 367 285 B1 | 5/1990 |
| EP | 0 411 714 A1 | 2/1991 |
| EP | 0 509 773 A1 | 10/1992 |
| GB | 1 465 127 | 2/1977 |

| | | | |
|---|---|---|---|
| GB | 2 139 099 A | | 11/1984 |
| WO | WO90/05518 | A1 | 5/1990 |
| WO | WO93/21982 | A1 | 11/1993 |
| WO | WO94/26229 | A1 | 11/1994 |
| WO | WO95/13108 | A1 | 5/1995 |
| WO | WO95/28193 | A1 | 10/1995 |
| WO | WO96/28215 | A1 | 9/1996 |
| WO | WO99/63926 | A1 | 12/1999 |
| WO | WO01/70332 | A1 | 9/2001 |
| WO | WO02/092169 | A1 | 11/2002 |

OTHER PUBLICATIONS

International Search Report and Written Opinion of PCT/US2004/027772 mailed on Mar. 11, 2005, 5 pages.

Ambu International A/S "Directions for use of Ambu® CardioPump™", 8 pages.

Christenson, J.M., "Abdominal Compressions During CPR: Hemodynamic Effects of Altering Timing and Force", The Journal of Emergency Medicine, vol. 10, pp. 257-266, 1992.

Cohen, Todd J. et al., "Active Compression-Decompression Resuscitation: a Novel Method of Cardiopulmonary Resuscitation", Department of Medicine and the Cardiovascular Research Institute, UC San Francisco, American Heart Journal 126(5):1145-1150, 1992.

Cohen, Todd J. et al., "Active Compression-Decompression: A New Method of Cardiopulmonary Resuscitation", JAMA 267(21): 2916-2923 (Jun. 3, 1992).

Dupuis, Yvon G., *Ventilators—Theory and Clinical Application*, pp. 447-448, 481, 496; Jan. 1986, Mosby Company.

Geddes, L.A. et al., "Inspiration Produced by Bilateral Electromagnetic, Cervical Phrenic Nerve Stimulation in Man," IEEE Transactions on Biomedical Engineering 38(9): 1047-1048 (Oct. 1991).

Geddes, L.A. et al., "Optimum Stimulus Frequency for Contracting the Inspiratory Muscles with chest Surface Electrodes to Produce Artificial respiration," Annals of Biomedical Engineering 18:103-108 (1990).

Geddes, L.A., "Electrically Produced Artificial Ventilation," Medical Instrumentation 22(5): 263-271 (1988).

Geddes, L.A., "Electroventilation—A Missed Opportunity?", Biomedical Instrumentation & Technology, Jul./Aug. 1998, pp. 401-414.

Glenn, William W.L. et al., "Diaphragm Pacing by Electrical Stimulation of the Phrenic Nerve," Neurosurgery 17(6): 974-984 (1985).

Glenn, William W.L., et al., "Twenty Years of Experience in Phrenic Nerve Stimulation to Pace the Diaphragm," Pace 9: 780-784 (Nov./Dec. 1986, Part I).

Kotze, P.L. et al., "Diaphragm Pacing in the Treatment of Ventilatory Failure,"San. Deel 68:223-224 (Aug. 17, 1995).

Laghi, Franco et al., "Comparison of Magnetic and Electrical Phrenic Nerve Stimulation in assessment of Diaphragmantic Contractility," American Physiological society, pp. 1731-1742 (1996).

Lindner, Karl H. et al., "Effects of Active Compression-Decompression Resuscitation on Myocardial and Cerebral Blood Flow in Pigs" Department of Anesthesiology and Critical Care Medicine, University of Ulm, Germany, Circulation 88(3):1254-1263, (Oct. 7, 1993).

Lurie, Keith G. et al., "Regulated to Death: The Matter of Informed Consent for Human Experimentation in Emergency Resuscitation Research," Cardiac Arrhythmia Center at the University of Minnesota, PACE 18:1443-1447 (Jul. 1995).

Mushin W. W. et al., "Automatic Ventilation of the Lungs—The Lewis-Leigh Inflating Valve," Blackwell Scientific, Oxford, GB, p. 838.

VOLUME EXCHANGER VALVE SYSTEM AND METHOD TO INCREASE CIRCULATION DURING CPR

CROSS REFERENCES TO RELATED APPLICATIONS

This application is a nonprovisional application claiming the benefit of U.S. Provisional Application No. 60/912,891, filed Apr. 19, 2007, the complete disclosure of which is herein incorporated by reference.

BACKGROUND OF THE INVENTION

This invention relates generally to the field of cardiopulmonary resuscitation, and in particular to techniques to increase circulation when performing CPR.

Despite current methods of CPR most people die after cardiac arrest. One of the major reasons is that blood flow to the heart and brain is very poor with traditional manual closed chest CPR. Greater circulation of blood during CPR will result in improved outcomes.

BRIEF SUMMARY OF THE INVENTION

In some embodiments, methods are described for regulating gas flows into and out of a patient. According to one method, respiratory gases are repetitively forced out of the lungs. Respiratory gases are also prevented from entering back into the lungs between chest compressions. Periodically, an oxygen-containing gas is supplied to the lungs to provide ventilation.

In one particular aspect, the gases are repetitively forced out of the lungs by repetitively compressing the chest and permitting the chest to recoil a rate of about 60 to about 120 times/min. In a further aspect, a low flow and volume of oxygen is continuously supplied to the lungs. This volume of oxygen is less than the volume of respiratory gases expelled with successive chest compressions so that the number of times that the lungs are expanded with oxygen-containing gases is reduced by the low level of continuous oxygen insufflation.

Other embodiments of this invention include methods and devices for increasing circulation during CPR by reducing the volume of air in the lungs during chest compressions so that the thorax has more space to permit more blood flow into the heart with each chest compression/chest recoil cycle. Such embodiments include ways to compress the chest and allow it to recoil. During each compression, air is pushed out of the lungs through a one way valve. Every time the chest wall recoils following a compression, air (or respiratory gases) from outside the patient is prevented from passively entering the lungs. With sequential compressions, less and less air remains in the thorax. This gradual extrusion of respiratory gases from the lungs with each chest compression results in more space within the thorax (lungs, blood vessels, and heart) to be filled with blood. With more blood in the chest and less air, each time the chest is compressed more blood is ejected from the heart. After some number of compressions, such as between about 12 and about 30 (depending upon how many people are performing CPR and if the airway is secured with a face mask versus and endotracheal tube or equivalent), air is allowed to actively enter the lungs either by the delivery of a positive pressure breath from a ventilation source or by negative pressure ventilation (e.g. an iron lung or equivalent).

One advantage of such techniques is that during the chest recoil, intracranial pressures are decreased more rapidly and to a lower value, thereby further increasing the duration and magnitude of cerebral perfusion pressure.

In one particular aspect, the volume of respiratory gas expelled over a series of chest compression/recoil cycles is in the range from about 1 to about 15 cc/kg. Also, the volume of respiratory gases expelled from the chest may be expelled against a low level of fixed or variable resistance that is in the range from about 0 cm H2O to about 10 cm H2O.

In a further embodiment, the invention provides an exemplary device to augment circulation during the performance of cardiopulmonary resuscitation in a patient in cardiac arrest. The device comprises a housing having a rescuer port and a patient port. A valve system is disposed in the housing. Further, the housing and the valve system are configured such that a volume of respiratory gas expelled from the lungs during each chest compression enters the housing through the patient port, passes through the valve system and exits the rescuer port. Also, when the chest wall recoils, oxygen containing gases are prevented from entering the lungs through the patient port by the valve system. A ventilation source may also be used to inject an oxygen-containing gas into the housing which passes through the valve system, through the patient port and to the patient to periodically expand the lungs with the oxygen-containing gases.

The valve system may be constructed using a variety of valves, such as check valves, spring valves, duck valves, electronically-controlled valves and the like. As another example, a pair of one way valves may be used that are separately configured to open with opposite gas flows passing through the housing. Also, a variety of ventilation sources may be used, such as mouth-to-mouth ventilation, a mouth-mask, a resuscitator bag, an automatic ventilator, a semi-automatic ventilator, a body cuirass, an iron-lung device and the like. In another aspect, the valve system may include a means to impede the exodus of respiratory gases from the lungs with a fixed or variable resistance that is in the range from about 0 cm $H_2O$ to about 10 cm $H_2O$.

In one particular arrangement, at least one physiological sensor may be used to measure one or more physiological parameters. Such sensors may include electrocardiogram signal sensors, impedance sensors to detect air/blood ratio in the thorax, and the like. Also, a communication system may be employed to permit signals from the physiological sensor(s) to be transmitted to a CPR device used during resuscitation to provide various types of feedback. This can include how to perform CPR, an optimal time to actively inflate the lungs with respiratory gases, an optimal time to defibrillate, and the like. Further, timing lights may be employed to assist a rescuer in performing CPR, such as when to provide chest compressions.

In a further aspect, a supply system may be used to deliver a low flow and volume of continuous oxygen into the lungs which is less than the volume of respiratory gases expelled with successive chest compressions. In this way, the number of times that the lungs are expanded with oxygen-containing gases is reduced by the low level of continuous oxygen insufflation.

In still another embodiment, the invention provides a device to augment circulation during the performance of cardiopulmonary resuscitation in a patient in cardiac arrest. The device comprises a housing having a rescuer port and a patient port. Means are provided for regulating gas flows through the housing such that a volume of respiratory gas expelled from the lungs during each chest compression enters the housing through the patient port and exits the rescuer port. Also, when the chest wall recoils, oxygen containing gases are prevented from entering the lungs through the patient port. A ventilation source is employed to inject an oxygen-containing gas into the housing and to pass through the patient port and to the patient to periodically expand the lungs with the oxygen-containing gases.

In one aspect, the means for regulating gas flows comprises a pair of one way valves that are separately configured to open with opposite gas flows through the housing.

DETAILED DESCRIPTION OF THE INVENTION

Figure 1:
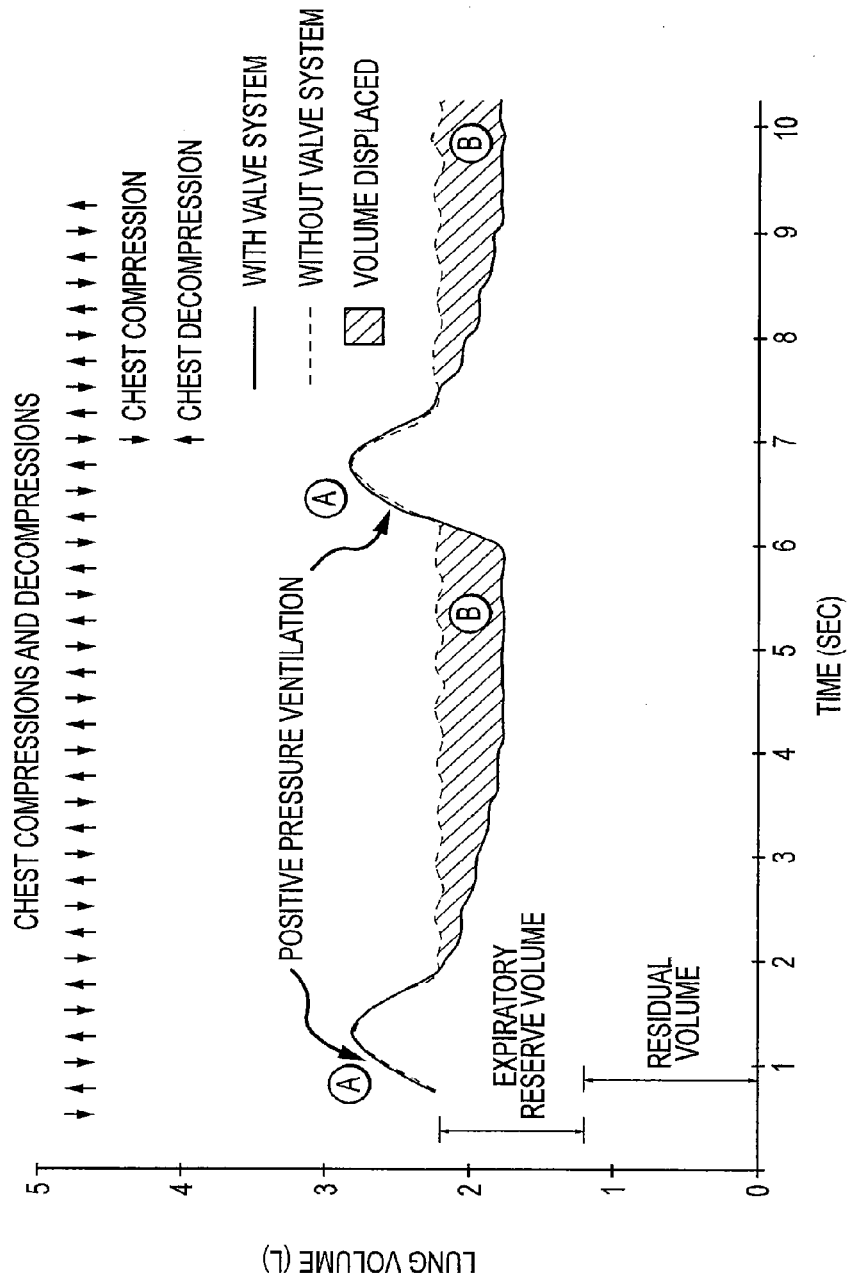
FIG. 1 is a graph illustrating lung volume while performing CPR when applying techniques according to the invention.

Multiple methods of chest compression may be used when performing CPR in patients in cardiac arrest. In this life-threatening situation, the heart is not capable of circulating blood so non-invasive external means are used to assist in the circulation of blood to the vital organs including the heart, lungs, and brain. The methods and devices that may be used to circulate blood during cardiac arrest include manual closed chest CPR, active compression decompression (ACD) CPR, mechanical CPR with manual or automated devices that compress the chest and either allow the chest to recoil passively or actively, and devices that compress the chest wall and then function like an iron lung and actively expand the thoracic cage. Some of these approaches and devices only compress the anterior aspect of the chest such as the sternum while other approaches and devices compress all or part of the thorax circumferentially. Some approaches and devices also compress the thorax and abdomen in an alternating sequence. Some approaches also involve compressing the lower extremities to enhance venous blood flow back to the heart and augment arterial pressure so that more blood goes to the brain. Some approaches also involve compressing the back, with the patient lying on his/her stomach. Some devices include both non-invasive methods and devices outlined above that are coupled with invasive devices, such as an intra-aortic balloon, and devices to simultaneously cool the patient Because the cardiac valves remain essentially intact during CPR, blood is pushed out of the heart into the aorta during the chest compression phase of CPR. When the chest wall recoils, blood from extrathoracic compartments (e.g. the abdomen, upper limbs, and head) enters the thorax, specifically the heart and lungs. Without the next chest compression, the blood would pool in the heart and lungs during cardiac arrest as there is insufficient intrinsic cardiac pump activity to promote forward blood flow. Thus, chest compressions are an essential part of CPR.

During the compression phase air is pushed out of the thorax and into the atmosphere via the trachea and airways. During the decompression phase it passively returns back into the thorax via the same airway system. As such, respiratory gases move out of and back into the thorax. With each compression the pressure within the chest is nearly instantaneously transmitted to the heart and also to the brain via the spinal column and via vascular connections. Thus, with each external chest compression pressure in the thorax and within all of the organs in the thorax is increased. Application of the methods and devices described in this application, in conjunction with any of the methods of CPR noted above, result in less and less air in the thorax, making room for more and more blood to return to the heart during the chest wall recoil phase. This increases circulation to the coronary arteries and lowers intracranial pressure during the chest wall decompression phase and with each subsequent compression increases blood flow to the vital organs, especially the brain. Since the delivery of oxygen is an important aspect of CPR, periodically a positive pressure ventilation needs to be delivered to inflate the lungs and provide oxygen. The lungs can also be inflated by periodic negative pressure ventilation with, for example, an iron lung or chest cuirass device. With both positive and negative pressure ventilation, typically a patient receives a tidal volume of about 500-1000 cc during each active ventilation (positive pressure ventilation). Thus, with the practice of this invention, an equal volume of respiratory gas is extruded from lungs over the course of several compressions so that after about 2 to 6 compressions the delivered volume has been removed from the thorax and its space can be replaced by blood that refills the thoracic space. This exchange is made possible by the fact that pressures within the thorax are transduced from one organ to another nearly instantaneously. This pressure transfer occurs between different thoracic compartments, for example the lungs and the right heart, very rapidly, especially between organs in the thorax with a high degree of compliance. For example, positive pressures are transferred during the compression phase from the lungs to the right heart, and as such right heart pressures are markedly increased with each chest compression. The increase in pressure within the lungs is transferred to the heart, propelling blood within the heart chambers in a forward direction along the course from right atrium to right ventricle to pulmonary artery pulmonary vein, left ventricle, and out the aorta. The inverse is also true, with chest wall recoil the negative pressures are transmitted throughout the thorax, including the spinal cord. This pulls blood into the heart and lungs from outside the thorax. The decreases in pressures within the thorax are augmented by the methods and devices described herein. The more gas that is pushed out of the lungs with each compression and not allowed back in, the more space is made available for blood to flow into the organs within the thorax each time the chest wall recoils. The volume of respiratory gas that is expelled over a series of chest compression/recoil cycles may be about 5 to about 15 cc/kg. It would typically be expelled after about 2 to 6 compression/recoil cycles. The volume of air expelled from the chest could be expelled against a low level of fixed or variable resistance, typically in the range from about 0 cm $H_2O$ to about 10 cm $H_2O$. This could be adjustable and could be provided by a valving system or other means having a low flow of positive pressure gases, such as oxygen. This process can be further augmented by active compressions and active decompressions. This process can also be further augmented by actively extracting a volume of respiratory gases between positive pressure breaths, creating even more space in the thorax to be filled with blood with each decompression phase of CPR to prime the heart for the next compression.

Periodically the lungs need to be inflated so that the pulmonary vascular resistance (blood pressure in the blood vessels in the lungs) does not get too high (which happens when the lungs are empty and collapse) which would limit blood flow through the lungs. Periodic inflation of the lungs also provides oxygen and helps to clear carbon dioxide. This process is depicted graphically in FIG. 1. The left-Y axis shows the volume of respiratory gas in the lungs in liters and the X axis shows time in seconds. At point A, a positive pressure breath is delivered. Down and up arrows show when chest compression and decompression (in this example passive chest wall recoil) occurs. Changes in the volumes of respiratory gases in the lungs when using the invention are shown by the solid line. With each chest compression air is pushed out of the lungs, and not allowed back into the lungs because of the valve system. This results in a progressive decrease in respiratory gases within the lungs. The shaded area, labeled B, is the volume of respiratory gas that is expelled from the lungs with each chest compression. The total volume, shown by B, creates space that is filled by more blood returning to the heart and lungs during the decompression phase whenever a positive pressure is not being applied to the thorax by chest compressions. By contrast, changes in the volumes of respiratory gases in the lungs without the invention are shown by the hashed line. Each compression and chest wall recoil cycle is associated with a slight increase and decrease in pressures in the airway as respiratory gases move freely into and out of the lungs with each decompression and compression cycle.

A variety of valves may be coupled to the patient's airway to permit respiratory gases to escape from the lungs during chest compressions, while permitting periodic ventilation. One type of valve could be a one-way valve, typically used in combination with another one-way valve that opens in the opposite direction and which is biased in the closed position so that gases cannot enter the lungs during chest recoil or chest decompression. Another valve system that may be used is described in U.S. Pat. Nos. 5,692,498; 6,062,219; 6,526,973; and 6,604,523, incorporated herein by reference. With such valves, the threshold cracking pressure could be set high enough so that respiratory gases were always prevented from entering into the lungs until actively ventilated.

Figure 2A:
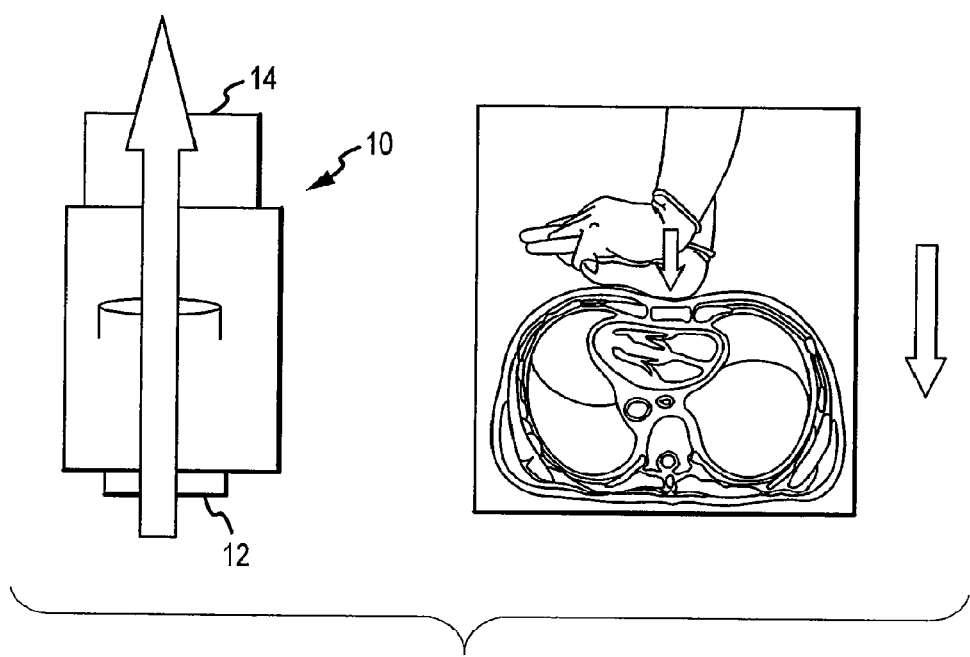
FIG. 2A schematically illustrates expired respiratory gases passing through a valve system during a chest compression according to the invention, along with a control system and a sensor.
Figure 2B:
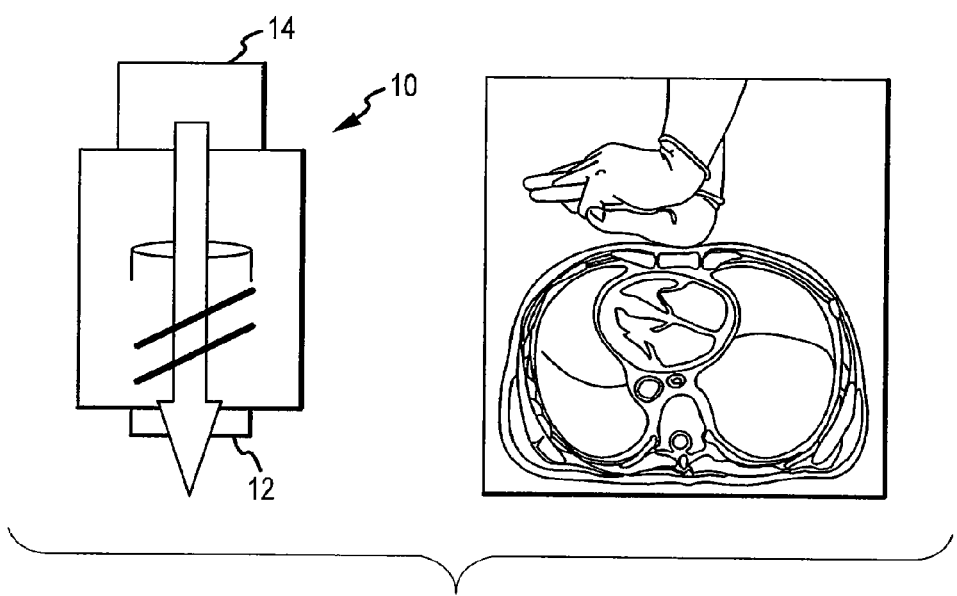
FIG. 2B schematically illustrates how respiratory gases are prevented from passing through the valve system and into the lungs during chest recoil or chest decompression according to the invention.
Figure 2C:
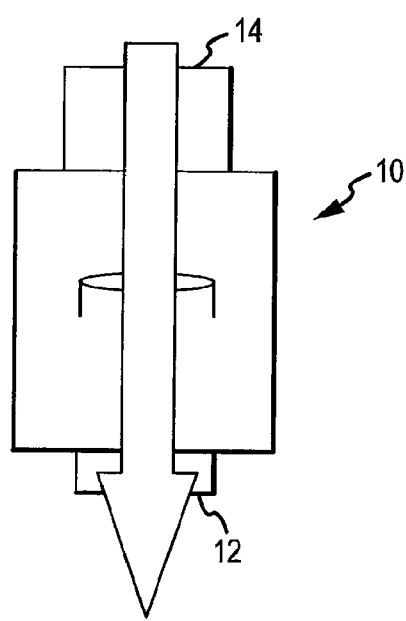
FIG. 2C schematically illustrates the injection of an oxygen-containing gas through the valve system to provide patient ventilation according to the invention.

Airflow into and out of the chest through one embodiment of the invention is shown schematically in FIGS. 2A-C. In FIG. 2A, a valve system 10 is schematically illustrated. Valve system 10 has a patient port 12 which interfaces with the patient's airway and a rescuer port 14 used by a rescuer to provide ventilation to the patient. When the chest is compressed (as illustrated by the hands pressing down on the chest wall), respiratory gases flow from the patient through the valve system 10 as shown by the arrow. In so doing, the respiratory gases pass into room air with minimal or no resistance from valve system 10. In FIG. 2B, the chest wall recoils during the decompression phase as the rescuer's hands are lifted. Now, valve system 10 prevents respiratory gases from entering the patient. In FIG. 2C a positive pressure ventilation is delivered through rescuer port 14 wherein passes through valve system 109 and out patient port 12 where is passes to the patient's lungs. As such, with each chest compression, more and more gases are forced out of the lungs. This is because during decompression, gases are prevented from entering. When needed, gases can be injected into the lungs to provide adequate ventilation.

Figure 2D:
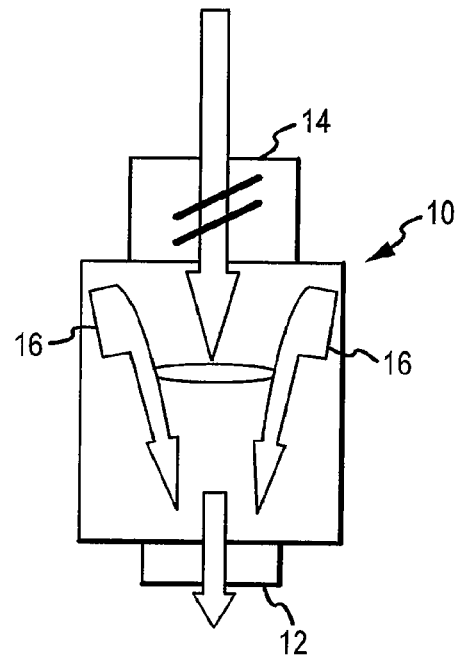
FIG. 2D schematically illustrates the passage of respiratory gases through a safety check valve if the patient inspires according to the invention.

In some cases, the patient may begin to breathe or gasp spontaneously. As shown in FIG. 2D, valve system 10 has one or more safety check valves 16 to permit gases to pass through patient port 12 and into the lungs. As one example, safety check valves 16 may be set to open at about −10 cm H2O. This schematic is not meant to be limiting but rather demonstrative of airflow through one potential embodiment of the invention during CPR.

The invention may employ a variety of techniques to enhance circulation. For example, a device to augment circulation during the performance of cardiopulmonary resuscitation in a patient in cardiac arrest may be configured to allow a volume of respiratory gas from the lungs to exit the airway with each external chest compression but prevents oxygen containing gases from passively reentering the lungs each time the chest wall recoils. This may be done using a valve system having a one-way valve and a means to periodically expand the lungs with oxygen-containing gases. Such a device may be particularly useful when the chest is compressed and allowed to recoil at a rate of about 60 to about 120 times/min. Such a device may also permit a volume of respiratory gases to be expelled from the lungs with each compression. Such a device can be used with manual CPR, manually operated CPR devices, or automated CPR devices. With each chest wall recoil, respiratory gases are prevented from returning to the lungs by means of a one-way valve. Over each successive chest compression/chest recoil cycle there is a successive decrease in respiratory gases within the lungs. Periodically, the lungs are actively expanded with oxygen-containing gas.

The valve system can be made of one or more check valves, spring valves, duck valves, other mechanical or electronically controlled valves and switches. The lungs are periodically expanded by a ventilation source that could include: mouth-mouth ventilation, mouth-mask, a resuscitator bag, an automatic or semi-automatic ventilator, a body cuirass or iron-lung like device or the like. A variety of sensors could be incorporated into the system to guide the ventilation rate and/or determine the degree of chest compression and/or degree of chest wall recoil including: airway pressure sensors, carbon dioxide sensors, and/or impedance sensors to detect air/blood ratio in the thorax to help guide ventilation and compression rate.

The valve system could include a one-way valve with a means to impede exhalation or the exodus of respiratory gases with a fixed or variable resistance. This could be in the range from about 0 to about 20 cm $H_2O$, and in some cases about 0 to about 10 cm H20. This may also be adjustable. In some cases such expiratory resistance helps to push blood out of the lungs back into the left heart, and serves as a means to help prevent buildup of blood in the lungs during CPR.

Figure 3A:
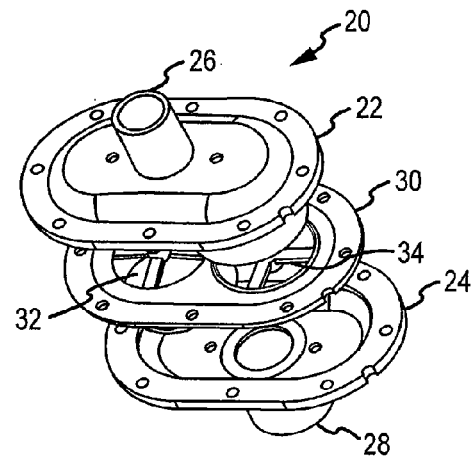
FIG. 3A illustrates one embodiment of a valve system according to the invention.

One particular embodiment of a valve system 20 is shown in FIG. 3A. Valve system 20 is constructed of a housing, which is conveniently manufactured as an inspiration interface housing 22 and a patient interface housing 24. A ventilation source port 26 for ventilation to the patient is included in housing 22 while a connector port 28 is included in housing 24. In this way, a ventilation source may be coupled to port 26 and port 28 may be used to interface with the patient, and the patient's airway. A valve plate 30 having a pair of one-way check valves 32 and 34 in between.

Figure 3B:
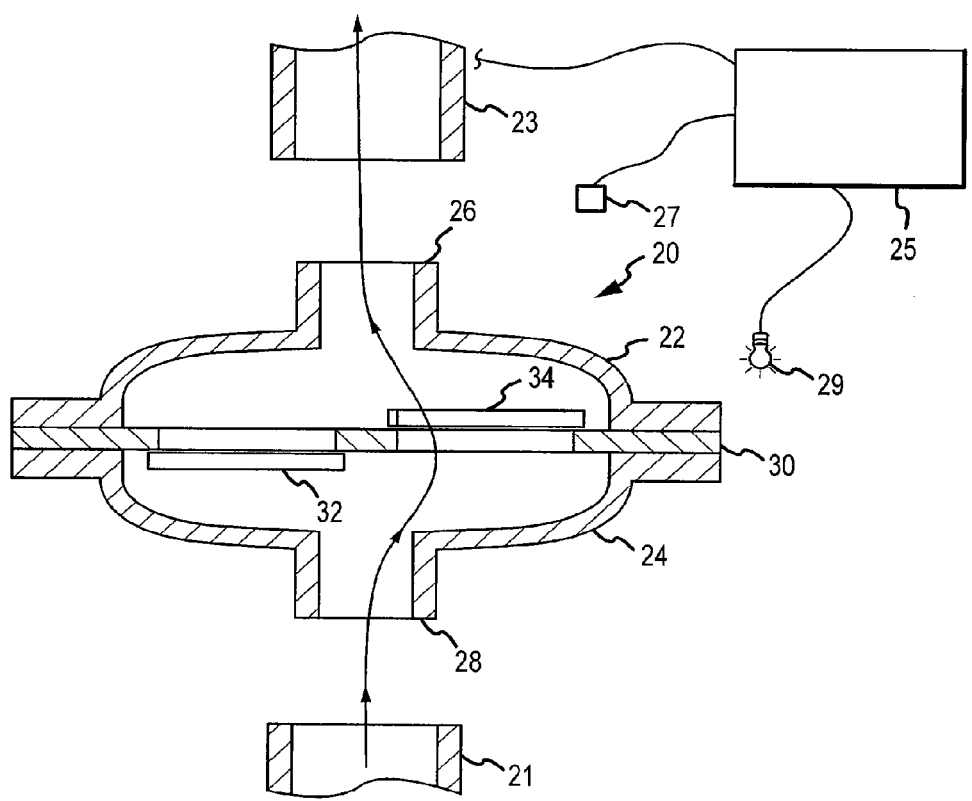
FIG. 3B is a cross sectional side view of the valve system of FIG. 3A illustrating gas flows with patient exhalation (such as during a chest compression), along with a control system and a sensor.

As shown in FIG. 3B, during chest compression, respiratory gases flow from the patient and pass through port 28 where the gases open expiratory check valve 34. From there, the gases exhaust to the atmosphere through port 26. Optionally, valve 34 may be biased in the closed position, and may open when the exiting gases exert a pressure that is less than about 20 cm H2O.

Port 28 may be coupled to a patient interface 21, which could include a facial mask, endotracheal tube, other airway device or any of the other interfaces described herein. Port 26 may be coupled to a ventilation source 23, such as a ventilatory bag, ventilator, tube for performing mouth-to-mouth resuscitation, or any of the other devices described herein.

Further, a controller 25 may be employed to control any of the electronic equipment. For example, if ventilation source 23 where a ventilator, controller 25 may be employed to control operation of the ventilator. One or more sensors 27 may be coupled to controller to monitor various physiological parameters of the patient as described herein. Also, controller 25 could modify application of chest compressions and/or ventilations based on the sensed parameters.

Controller 25 may also be coupled to one or more timing lights 29 which could be used to indicate to a rescuer as to when to provide chest compressions and/or ventilations.

Figure 3C:
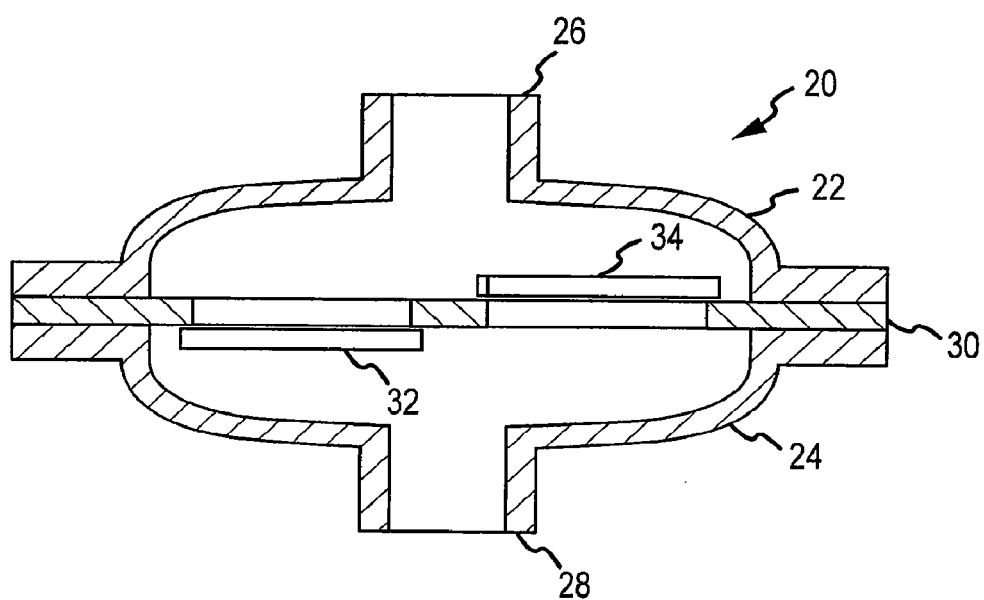
FIG. 3C is a cross sectional side view of the valve system of FIG. 3A illustrating the absence of gas flow when the patient's chest recoils or is lifted.
Figure 3D:
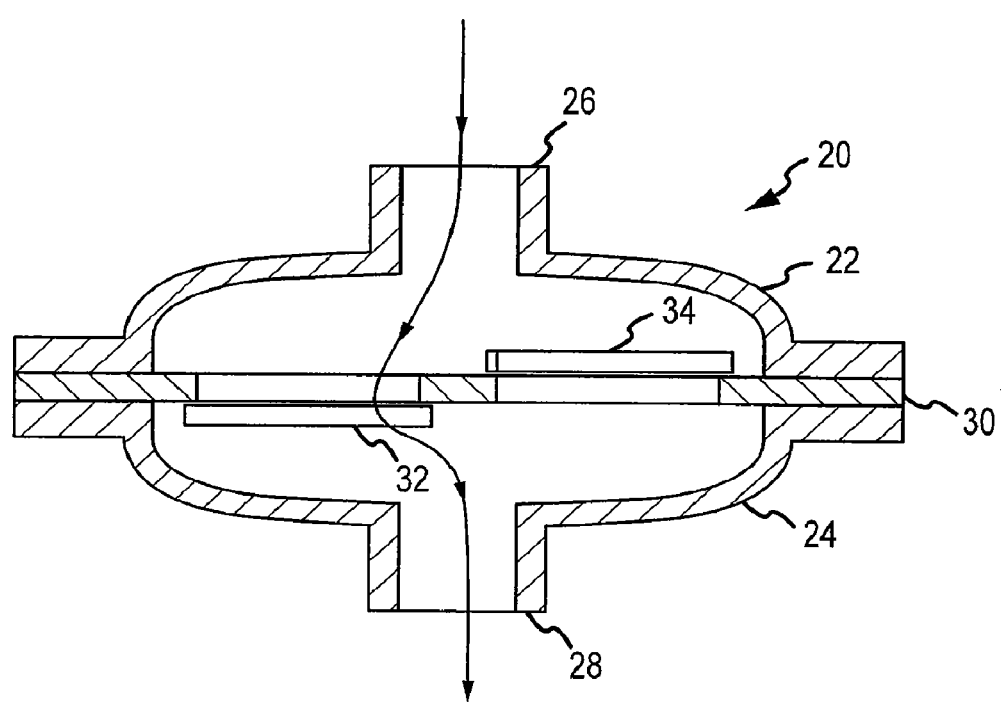
FIG. 3D is a cross sectional side view of the valve system of FIG. 3A illustrating gas flows when delivering an oxygen-containing gas to the patient.

In FIG. 3C, the chest wall recoils. Inspiratory check valve 32 is biased in the closed position, by use of a spring, elastomer or the like, so that no respiratory gases are allow through inspiratory check valve 32. Valve 32 may be biased closed until a pressure in the range of about −5 to about −10 mmHg is achieved. This is most likely to occur when the patient takes a spontaneous gasp during CPR, and then airflow moves through the inspiratory check valve 32 to the patient through port 28. This can also occur if a rescuer ventilates the patient rapidly with a large tidal volume rapidly through port 26 as shown in FIG. 3D.

Any of the valve systems described herein could also include or be associated with physiological sensors, timing lights, impedance sensors to detect air/blood ratio in the thorax, and a way to communicate with a CPR device or other apparatus used during resuscitation (e.g. defibrillator) to provide feedback in terms of how to perform CPR, the optimal time to actively inflate the lungs with respiratory gases or the optimal time to defibrillate.

The valve systems or associated devices could also include a way to deliver a low flow and volume of continuous oxygen into the lungs which is less than or just equal to the total volume of the expelled volume of respiratory gases with chest compressions so that the number of times that the lungs are expanded with oxygen-rich gases is reduced by the low level of continuous oxygen insufflation.

Figure 4:
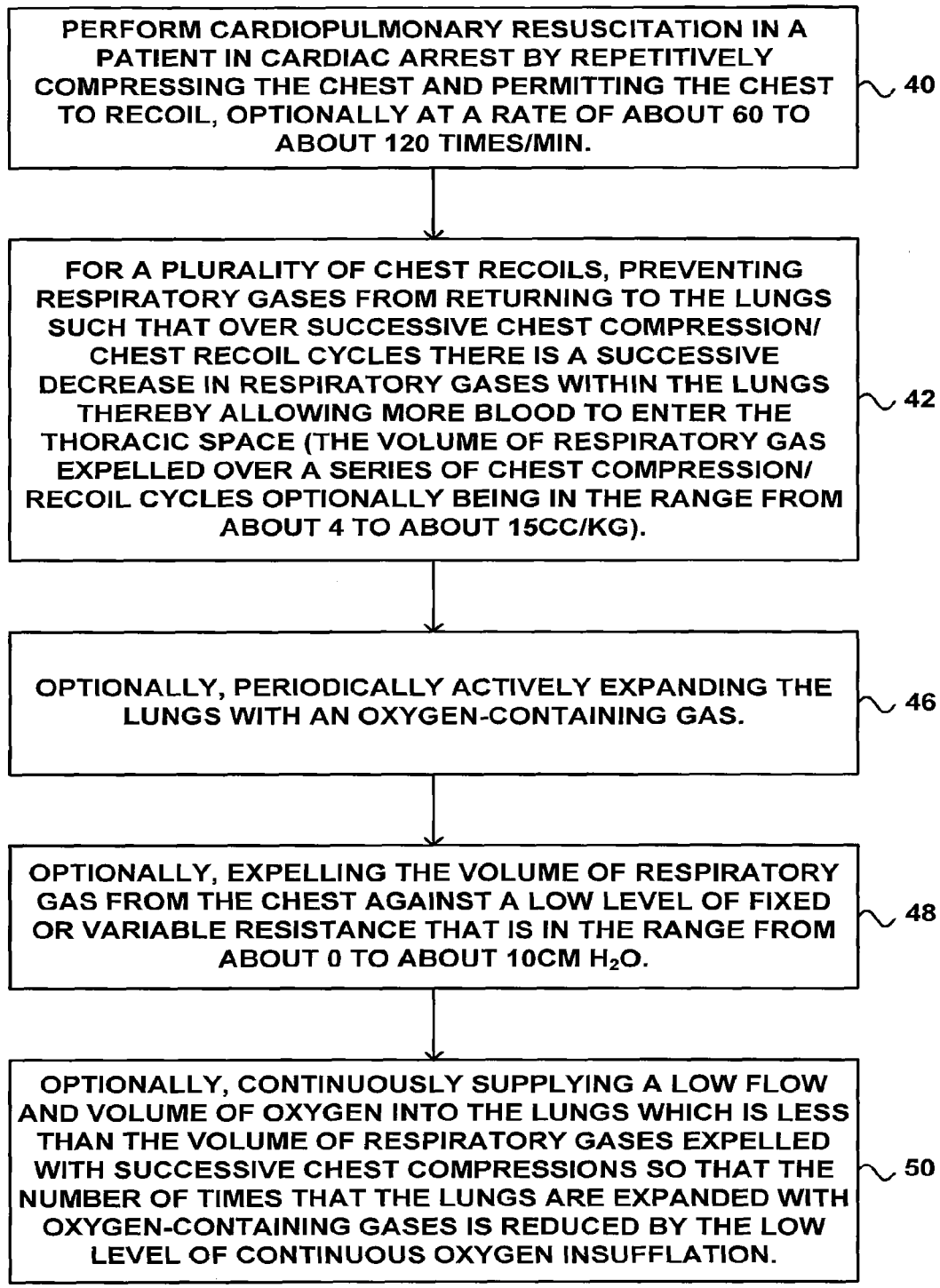
FIG. 4 is a flow chart illustrating one method for performing CPR according to the invention.

One exemplary method for controlling gas flow into and out of a patient's lungs is illustrated in FIG. 4. At step 40, cardiopulmonary resuscitation is performed on a patient in cardiac arrest. This may be performed by compressing the chest and allowing the chest to recoil at a rate of about 60 to about 120 times/min.

For a plurality of chest recoils, respiratory gases are prevented from returning to the lungs such that over successive chest compression/chest recoil cycles there is a successive decrease in respiratory gases within the lungs (see step 42). This allows more blood to enter the thoracic space (the volume of respiratory gas expelled over a series of chest compression/recoil cycles optionally being in the range from about 4 to about 15 cc/kg). Hence, over each successive chest compression/chest recoil cycle there is a successive decrease in respiratory gases within the lungs thereby allowing more blood to enter the thoracic space.

Periodically, the patient may be ventilated (see step 46), such as by periodically actively expanding the lungs with an oxygen-containing gas. During the chest recoil phase of CPR, intracranial pressures are decreased more rapidly and to a lower value thereby further increasing the duration and magnitude of cerebral perfusion pressure. Optionally, the volume of respiratory gas expelled from the chest may be expelled against a low level of fixed or variable resistance that is in the range from about 0 to about 10 cm H2O (see step 48).

The devices and methods described herein may be used with any type of CPR technique that involves manipulation of the chest to change pressures within the thorax would benefit from this improved method of invention. Also, the method for providing periodic expansion of the lungs could include mouth-mouth ventilation, a resuscitator bag, an automatic or semi-automatic ventilator, a body cuirass or iron-lung like device. The method could also include a way to deliver a low flow and volume of continuous oxygen into the lungs which is less than the total volume of the expelled volume of respiratory gases so that the frequency of positive pressure ventilations by an external ventilation source could be reduced by the low level of continuous oxygen insufflation (see step 50).

A variety of sensors could be used to guide the periodic ventilation rate or determine the degree of chest compression or degree of chest wall recoil. Sensors could include airway pressure sensors, timing lights, carbon dioxide sensor, electrocardiogram signal sensors, and/or impedance sensors to detect air/blood ratio in the thorax to help guide ventilation and compression rate and determine if CPR should be continued, the optimal time and way to defibrillate, and when to stop CPR efforts because of futility.

The method could include a number of different airway adjuncts to maintain a seal between the trachea and the ventilation source or pharynx and ventilation source or mouth and ventilation source (e.g. endotracheal tube, face mask, laryngeal mask airway, supraglottic airway, and the like). Sensors within these airways could be used to verify proper airway adjunct placement. Such sensors could include a carbon dioxide detector which could be housed in a manner that is protected from bodily fluids.

The method could include a means to transmit the amount of respiratory gas volume delivered or expelled from the chest to a monitoring system that could be used as part of a closed loop circuit to maximize the number of compressions interspersed between active ventilations in order to maximize circulation during CPR. Circulation during CPR could be measured by a variety of means including measurement of end tidal carbon dioxide, the change in expired end tidal carbon dioxide levels over a given time interval, a change in impedance within the body, and changes in other physiological parameters such as temperature.

The invention has now been described in detail for purposes of clarity and understanding. However, it will be appreciated that certain changes and modifications may be practiced within the scope of the appended claims.

What is claimed is:

1. A device to augment circulation during the performance of cardiopulmonary resuscitation in a patient in cardiac arrest, the device comprising:
   a housing having a rescuer port and a patient port, an exhalation one way valve and an inhalation one way valve which is biased in a closed position;
   wherein the housing and one way valves are configured such that a volume of respiratory gas expelled from the lungs during each chest compression enters the housing through the patient port, passes through the exhalation one way valve and exits the rescuer port, and wherein, when the chest wall recoils, oxygen containing gasses are prevented from entering the lungs through the rescuer port by both of the one way valves;

a ventilation source to inject an oxygen-containing gas into the housing, to open the inhalation one way valve, and to pass through the rescuer port and to the patient to periodically expand the lungs with the oxygen-containing gases; and wherein the inhalation one way valve is configured to remain closed during multiple, successive chest decompressions so that respiratory gasses are prevented from reaching the lungs through the inhalation one way valve over successive chest compression/chest recoil cycles to successively decrease the volume of respiratory gasses in the lungs thereby allowing more blood to enter the thoracic space.

2. A device to augment circulation during the performance of cardiopulmonary resuscitation in a patient in cardiac arrest, the device comprising:

a housing having a rescuer port and a patient port;

a valve system disposed in the housing;

wherein the housing and the valve system are configured such that a volume of respiratory gas expelled from the lungs during each chest compression enters the housing through the patient port, passes through the valve system and exits the rescuer port, and wherein, when the chest wall recoils, oxygen containing gases are prevented from entering the lungs through the patient port by the valve system;

a ventilation source to inject an oxygen-containing gas into the housing, to pass through the valve system, and to pass through the patient port and to the patient to periodically expand the lungs with the oxygen-containing gases;

at least one physiological sensor that is selected from a group consisting of airway pressure sensors, carbon dioxide sensors, electrocardiogram signal sensors, impedance sensors to detect air/blood ratio in the thorax and a communication system to permit signals from the physiological sensor to be transmitted to a CPR device used during resuscitation to provide feedback for at least one of how to perform CPR, an optimal time to actively inflate the lungs with respiratory gases and an optimal time to defibrillate, and further comprising timing lights that are configured to light to assist a rescuer in performing CPR.

3. A device as in claim 2, wherein the valve system includes at least one valve selected from a group consisting of a check valve, a spring valve, a duck valveand an electronically-controlled valve.

4. A device as in claim 2, wherein the ventilation source is selected from a group consisting of mouth-to-mouth ventilation, a mouth-mask, a resuscitator bag, an automatic ventilator, a semi-automatic ventilator, a body cuirass and an iron-lung device.

5. A device as in claim 2, wherein the valve system includesa means to impede the exodus of respiratory gases from the lungs with a fixed or variable resistance that is in the range from about 0 to about 10 cm $H_2O$.

6. A device as in claim 2, further comprising a supply system to deliver a low flow and volume of continuous oxygen into the lungs which is less than the volume of respiratory gases expelled with successive chest compressions so that the number of times that the lungs are expanded with oxygen-containing gases is reduced by the low level of continuous oxygen insufflation.

7. A device as in claim 2, wherein the valve system comprises a pair of one way valves that are separately configured to open with opposite gas flows through the housing.

8. A device to augment circulation during the performance of cardiopulmonary resuscitation in a patient in cardiac arrest, the device comprising:

a housing having a rescuer port and a patient port;

means for regulating gas flows through the housing, wherein the means for regulating is configured such that a volume of respiratory gas expelled from the lungs during each chest compression enters the housing through the patient port and exits the rescuer port, and wherein, when the chest wall recoils, oxygen containing gases are prevented from entering the lungs through the patient port; and a ventilation source to inject an oxygen-containing gas into the housing and to pass through the patient port and to the patient to periodically expand the lungs with the oxygen-containing gases; wherein the means for regulating is further configured to prevent oxygen containing gases from reaching the lungs through the patient port over multiple, successive chest compressions and recoils such that a volume of at least about 4 cc/kg to about 15 cc/kg of respiratory gasses are expelled from the lungs but not replaced while performing cardiopulmonary resuscitation.

9. A device as in claim 8, wherein the means for regulating gas flows comprises a pair of one way valves that are separately configured to open with opposite gas flows through the housing.

10. A device as in claim 1, further comprising a monitoring system to measure the total volume expelled from the lungs while performing CPR.

11. A device as in claim 8, further comprising a monitoring system to measure the total volume expelled from the lungs while performing CPR.

* * * * *